United States Patent [19]

Shroff

[11] 4,027,019

[45] May 31, 1977

[54] 3-OXIMES OF D-17α-ETHYNYL-19-NORTESTOSTERONE ESTERS AND METHOD

[75] Inventor: Arvin Pranlal Shroff, Piscataway, N.J.

[73] Assignee: Ortho Pharmaceutical Corporation, Raritan, N.J.

[22] Filed: Jan. 23, 1976

[21] Appl. No.: 652,000

Related U.S. Application Data

[63] Continuation-in-part of Ser. No. 598,966, July 24, 1975, abandoned.

[52] U.S. Cl. .......................... 424/238; 260/397.4; 260/397.5
[51] Int. Cl.² ......................................... C07J 1/00
[58] Field of Search .................. 260/397.4, 397.5

[56] References Cited

UNITED STATES PATENTS

| 3,532,689 | 10/1970 | Shroff | 260/239.55 |
| 3,780,073 | 12/1973 | Shroff | 260/397.5 |
| 3,912,768 | 10/1975 | Gardi et al. | 260/397.5 |

OTHER PUBLICATIONS

"Steroids," Dec. 1963, pp. 732–737, by Edgren et al.

*Primary Examiner*—Elbert L. Roberts
*Attorney, Agent, or Firm*—Benjamin F. Lambert

[57] ABSTRACT

3-Oximes of D-17α-ethynyl-19-nortestosterone esters and derivatives thereof have pre- and post-coital activity for the suppression of fertility.

19 Claims, No Drawings

3-OXIMES OF D-17α-ETHYNYL-19-NORTESTOSTERONE ESTERS AND METHOD

This is a continuation-in-part of pending application U.S. Ser. No. 598,966, filed July 24, 1975, and now abandoned.

BACKGROUND OF THE INVENTION

In my U.S. Pat. No. 3,780,073, which is incorporated herein by reference, the esters of the 3-oximes of DL-17α-ethynyl-19 nortestosterone and its derivatives having post-coital activity for the supression of fertility are described. Because it is generally desirable to administer the smallest effective dose of any drug, especially a steroid, considerable effort has been expended to resolve these esters in the expectation that the activity resides chiefly in one isomer. Thus it would be possible to administer a smaller dose of the active isomer and achieve the same result as a larger dose of the racemate. Prior to the present invention the active D-isomers have not existed free of the L-isomers. I have now found a method for preparing the D-isomers of said esters (wherein the activity of the racemic mixture chiefly resides) as pure chemical compounds free of the L-isomers.

SUMMARY OF THE INVENTION

The present invention relates to certain esters in the D series of the 3-oximes of 17α-ethynyl-19-nortestosterone and its derivatives, to a method for preparing the esters, and to a method of suppressing fertility by administration thereof to a female animal.

The novel compounds of the present invention are represented by the formula:

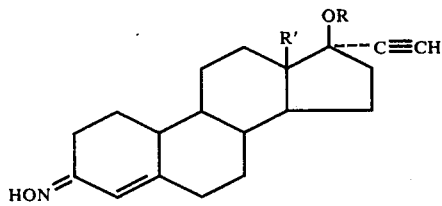

(I)

wherein R is alkanoyl of from 2 to 10 carbon atoms such as acetyl, propionyl, butyryl, pentanoyl, octanoyl, and the like, and R' is a member selected from the group consisting of methyl and ethyl. The preferred compound of the invention is that wherein R' is ethyl and R is acetyl.

The compounds of the invention possess valuable pharmacological activity as antifertility agents, and more particularly as agents for the suppression of fertility when given post-coitally. They are also suitable as long-acting compounds for the suppression of fertility when administered parenterally, especially pre-coitally. They may be administered orally or by any suitable parenteral means, intramuscular and subcutaneous administration being preferred. The compounds of the invention are effective when given pre-coitally in doses of from about 0.1 to about 1.0 mg/kg/day (preferably from about 0.1 to about 0.5 mg/kg/day) and when given post-coitally in doses of from about 10 to about 20 mg/kg/day.

The compounds of the present invention may be employed in combination with other pharmacologically active compounds such as, for example, estrogens like ethinylestradiol, mestranol, 17α-ethinylestradiol 3-cyclopentyl ether, 17β-estradiol as well as conjugated estrogenic hormones. The combination of an estrogenic compound and a progestational steroid often results in more effective control of the menstrual cycle by lowering the incidence of certain side effects such as breakthrough bleeding and spotting often associated with progestins. The estrogen and progestational steroid may be employed in ratios of from about 0.050 mg of the progestational steroid and about 0.015 mg of estrogen to about 0.50 mg of progestational steroid and about 0.075 mg of estrogen. The preferred ratio is about 0.125 mg of progestin to about 0.035 mg of estrogen.

While it was expected that the active D-isomers would be about twice as potent as their respective racemates, it has surprisingly been discovered that the D-isomers are about ten times as potent as their corresponding racemates. This surprising and unexpected leap in potency is in no way suggested or predicted by the activity of the prior art compounds.

The compounds of the invention may be prepared by reacting a 3-ketone in the D series of formula:

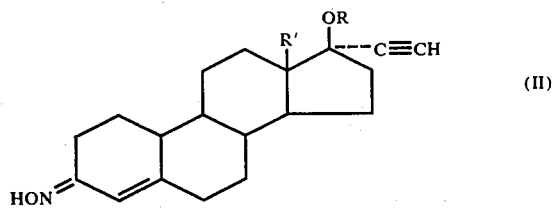

(II)

wherein R and R' are as previously defined with an hydroxylamine hydrohalide such as hydroxylamine hydrochloride and the like in the presence of a base such as pyridine, aqueous sodium hydroxide, aqueous sodium acetate, and the like to form the corresponding 3-oxime in the D series of formula (I).

The 3-ketone in the D series of formula (II) may be prepared by reacting a compound in the D series of formula:

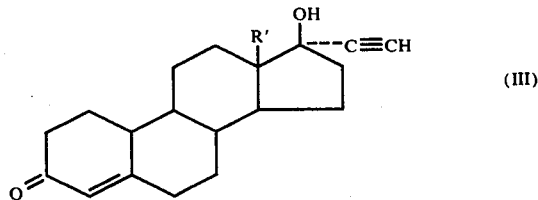

(III)

wherein R' is as previously defined, with an appropriate acid anhydride such as acetic anhydride, propionic anhydride, butyric anhydride, caprylic anhydride and the like, to form a diester in the D series of formula:

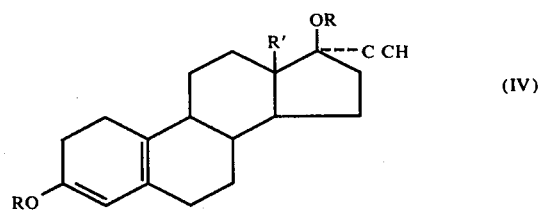

(IV)

which is then converted by treatment with a suitable base such as an alkali metal hydroxide into the monoester ketone in the D series of formula (II). This preparation of compound (II) is described for the DL compounds in Belgian Patent No. 5.529M. The D series starting materials of formula (III) are generally known or may be prepared by methods known in the art.

The invention may be illustrated by the following examples:

EXAMPLE I

D-17β-Acetoxy-13β-ethyl-17α-ethynyl-gon-4-en-3-one oxime:

A solution of 4.5 g of D-17β-acetoxy-13β-ethyl-17α-ethynyl-gon-4-en-3-one in 15 ml of pyridine and 2.0 g of hydroxylamine hydrochloride is heated on a steam bath for 45 minutes. It is then cooled and poured into a large amount of ice-water, after which the solid which is thus produced is filtered off and air dried. Recrystallization from methylene chloride-ethanol gives D-17β-acetoxy-13β-ethyl-17α-ethynyl-gon-4-en-one oxime, m.p. 214°–218° C.; $\alpha_D^{25}+''°$.

In like manner, substituting an equivalent amount of the appropriately substituted oxime for the D-17β-acetoxy-13β-ethyl-17α-ethynyl-gon-4-en-3-one used above, there are prepared:

D-17β-caproyloxy-13β-ethyl-17α-ethynyl-gon-4-en-3-one oxime;

D-17β-decanoyloxy-17α-ethynyl-19-norandrost-4-en-3-one oxime;

D-17α-ethynyl-17β-propionyloxy-19-norandrost-4-en-3-one oxime.

EXAMPLE II

D-3,17β-Diacetoxy-13β-ethyl-17α-ethynyl-gon-3,5(10)-diene:

A mixture of 1.0 g of D-13β-ethyl-17α-ethynyl-gon-4-en-17β-ol-3-one, 16 ml of acetic anhydride, 4 ml of acetyl chloride, and 0.4 ml of pyridine is heated at reflux for 3 hours, after which the solvents are removed by evaporation in vacuo. The resulting residue is dissolved in benzene, and the solution is washed with water and brine and dried. The benzene is removed and, upon trituration with ether in an ice-bath, crystals of D-3,17β-diacetoxy-13β-ethyl-17α-ethynyl-gon-3,5(10)-diene are obtained; m.p. 144°–150° C.

In like manner, substituting equivalent amounts of an appropriately substituted alcohol and an appropriate acid anhydride for the D-13β-ethyl-17α-ethynyl-gon-4-en-17α-ol-3-one and acetic anhydride used above, there are prepared:

D-3,17β-dicaproyloxy-13β-ethyl-17α-ethynyl-gon-3,5(10)-diene;

D-3,17β-didecanoyloxy-17α-ethynyl-19-norandrost-3,5(10)-diene;

D-3,17β-dipropionyloxy-17α-ethynyl-19-norandrost-3,5(10)-diene.

EXAMPLE III

D-17β-Acetoxy-13β-ethyl-17α-ethynyl-gon-4-en-3-one:

To a solution of 0.35 g of D-3,17β-diacetoxy-13β-ethyl-17α-ethynyl-gon-3,5(10)-diene in 60 ml of methanol and 10 ml of tetrahydrofuran is added 10 ml of a 2% methanolic solution of potassium hydroxide. After the addition, the mixture is stirred for one hour at 0° C under a nitrogen atmosphere, after which it is poured into 400 ml of brine and neutralized with 10% hydrochloric acid. After isolation of this product in ether, one obtains the desired D-17β-acetoxy-13β-ethyl-17α-ethynyl-gon-4-en-3-one; m.p. 162°–164° C.

In like manner, substituting an equivalent amount of an appropriately substituted diene for the D-3,17β-diacetoxy-13β-ethyl-17α-ethynyl-gon-3,5(10)-diene used above, there are prepared D-17β-caproyloxy-13β-ethyl-17α-ethynyl-gon-4-en-3-one;

D-17β-decanoyloxy-17α-ethynyl-19-norandrost-4-en-3-one;

D-17α-ethynyl-17β-propionyloxy-19-norandrost-4-en-3-one.

EXAMPLE IV

The antilittering effect of the compounds of the invention is determined by the following test. In each case the test material is D-17β-acetoxy-13β-ethyl-17α-ethynyl-gon-4-en-3-one oxime.

A. Antiovulatory Efficacy in Rats

Vaginal smears were obtained daily from adult female rats for evidence of normal 4-day estrous cycles. Selected rats in diestrous were treated with the test material administered intragastrically in 0.5 cc sesame oil, and again on the following day when the animals were in proestrous. The animals were sacrificed the next day, at which time they would normally have ova in the proximal segment of the fallopian tubes. Oviducts were separately flushed with saline onto a glass microscope slide. The tubal flushings were examined with a binocular microscope; if ova were present their condition and number were noted.

The test material had antiovulatory properties in rats at dosages as low as 0.5 mg/kg when administered orally for the two days preceding an expected ovulation. Five rats were tested at each dose level, and no ova were detected in tubal washings after treatment with doses of at least 0.5 mg/kg. At 0.25 mg/kg, 4 of 5 treated rats had normal ova in the reproductive tract. The fifth rat failed to ovulate (Table 1).

Table 1

| Dose mg/kg/day | Number Treated | Number Ovulating |
| --- | --- | --- |
| 0 | 5 | 4 |
| 0.25 | 5 | 4 |
| 0.5 | 5 | 0 |
| 1.0 | 5 | 0 |

For comparison, use of DL-17βacetoxy-13β-ethyl-17β-ethynyl-gon-4-en-3-one oxime as the test material requires administration of at least 5.0 mg/kg to obtain any significant antiovulatory effect--ten times as much as the D isomer (Table 1A)

TABLE 1A

| Dose mg/kg/day | Number Treated | Number Ovulating |
| --- | --- | --- |
| 1.0 | 5 | 4 |
| 5.0 | 5 | 2 |
| 10.0 | 5 | 0 |

B. Interruption of Early Pregnancy in Rats

Adult female rats were examined daily for vaginal cytology. Those animals exhibiting proestrous smears were cohabited overnight with fertile male rats (1 male/1 female) and examined the following morning for vaginal cytology and the presence of sperm in vaginal washings. The day that sperm were observed in vaginal washings was considered to be day 1 of gestation. The test material was administered by gavage in sesame oil on days 1 through 6 of gestation, and the rats were killed on day 14 for examination of uterine contents.

When adult rats were treated orally with the test material during the first 6 days of gestation, implantation was prevented. This effect occurred at dosages of 10 to 20 mg/kg. Fertility inhibition was complete at 10 mg/kg where, although 1 of 7 rats showed evidence of implantation, there was only one nidus and it was resorbing (Table 2).

Table 2

| Dose mg/kg/day | Number Treated | Number with Implants | Number of Implants Normal | Resorbed |
|---|---|---|---|---|
| 0 | 5 | 5 | 65 | 8 |
| 5 | 7 | 5 | 42 | 8 |
| 10 | 7 | 1 | 0 | 1 |
| 20 | 7 | 0 | — | — |

For comparison, administration of 10.0 mg/kg of DL-17β-acetoxy-13β-ethyl-17α-ethynyl-gon-4-en-3-one oxime as the test material is not effective in inhibiting fertility (Table 2A).

TABLE 2A

| Dose mg/kg/day | Number Treated | Number with Implants | Number of Implants Normal | Resorbed |
|---|---|---|---|---|
| 1.0 | 5 | 4 | 61 | 0 |
| 5.0 | 5 | 5 | 87 | 0 |
| 10.0 | 5 | 5 | 62 | 0 |

It must be stressed that the test material used above is at least ten times more active than its racemate in its antiovulatory properties in rats. Further, the test material is effective in interrupting early pregnancy in rats at a dose at which the racemate is totally ineffective for this purpose. These unexpected results exemplify the utility of the present invention, which is defined in the following claims.

What is claimed is:

1. A compound in the D series of the formula:

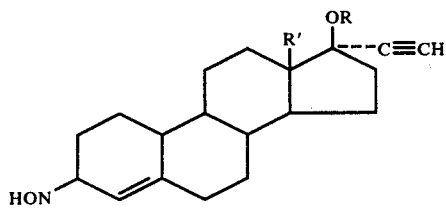

wherein R is alkanoyl of from 2 to 10 carbon atoms and R' is a member selected from the group consisting of methyl and ethyl.

2. The compound of claim 1 wherein R' is ethyl.
3. The compound of claim 2 wherein R is caproyl.
4. The compound of claim 2 wherein R is acetyl.
5. The compound of claim 2 wherein R is propionyl.
6. The compound of claim 2 wherein R is decanoyl.
7. The compound of claim 1 wherein R' is methyl.
8. The compound of claim 7 wherein R is acetyl.
9. A method of preparing a compound in the D series of claim 1 of the formula:

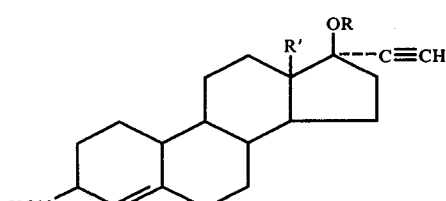

which comprises reacting a ketone in the D series of formula:

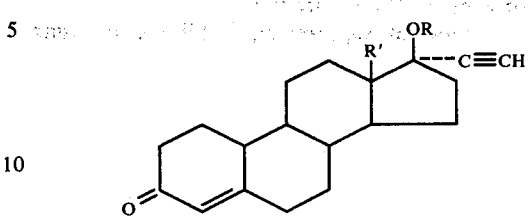

with an hydroxylamine hydrohalide in the presence of a base, wherein R is alkanoyl of from 2 to 10 carbon atoms and R' is a member selected from the group consisting of methyl and ethyl.

10. The method as in claim 9, wherein the base is a member selected from the group consisting of pyridine, sodium hydroxide, and sodium acetate.

11. The method of claim 9 wherein the hydroxylamine hydrohalide is hydroxylamine hydrochloride.

12. The method as in claim 9, wherein R is acetyl and R' is ethyl.

13. A method of suppressing fertility comprising administering to a female animal an effective antifertility amount of a compound in the D series of claim 1 of formula:

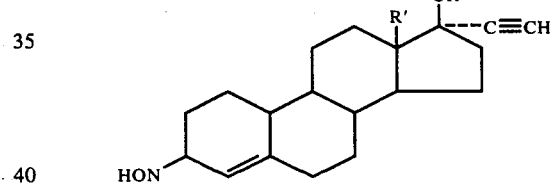

wherein R is alkanoyl of from 2 to 10 carbon atoms and R' is a member selected from the group consisting of methyl and ethyl, whereby fertility is suppressed.

14. The method of claim 13 wherein R is acetyl and R' is ethyl.

15. A composition useful in suppressing fertility comprising a compound in the D series of claim 1 of formula:

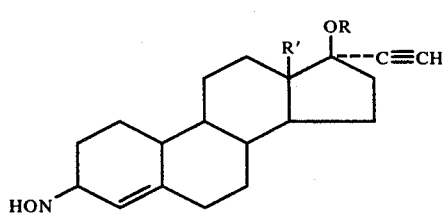

and an estrogenic hormone, wherein R is alkanoyl of from 2–10 carbon atoms and R' is a member selected from the group consisting of methyl and ethyl.

16. The composition of claim 15 wherein R is acetyl, R' is ethyl and the estrogenic hormone is selected from the group consisting of ethinylestradiol, 17β-estradiol, mestranol and 17α-ethinylestradiol 3-cyclopentyl ether.

17. The composition of claim 16 wherein the estrogenic hormone is ethinylestradiol.

18. A method of suppressing fertility comprising administering to a female an effective antifertility amount of a composition of claim 15.

19. The method of claim 18 wherein R is acetyl, R' is ethyl and the estrogenic hormone is ethinylestradiol.

* * * * *

UNITED STATES PATENT AND TRADEMARK OFFICE
CERTIFICATE OF CORRECTION

PATENT NO. : 4,027,019
DATED : May 31, 1977
INVENTOR(S) : Arvin Pranlal Shroff

It is certified that error appears in the above-identified patent and that said Letters Patent are hereby corrected as shown below:

In Column 3, line 20, "$\alpha_D^{25} + 11°.$" should read "$\alpha_D^{25} + 41°.$"

Signed and Sealed this

Twenty-first Day of February 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE

CERTIFICATE EXTENDING PATENT TERM
UNDER 35 U.S.C. 156

Patent No.     : 4,027,019

Dated          : May 31, 1977

Inventor(s)    : Arvin P. Shroff

Patent Owner   : Ortho Pharmaceutical Corporation

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

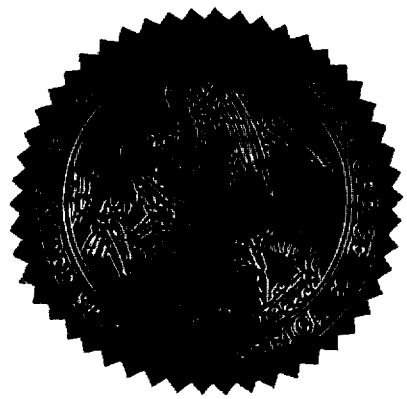

I have caused the seal of the Patent and Trademark Office to be affixed this 8th day of February, 1991.

Harry F. Manbeck, Jr.
Assistant Secretary and Commissioner
of Patents and Trademarks